United States Patent [19]

Holoch et al.

[11] Patent Number: 4,987,264
[45] Date of Patent: Jan. 22, 1991

[54] NOVEL POLYPHENOL AND THERMOSETTING PLASTICS PREPARED THEREFROM

[75] Inventors: Jan Holoch, Leimen; Roland Peter, Mutterstadt; Philipp Eisenbarth; Thomas Allspach, both of Bad Duerkheim, all of Fed. Rep. of Germany

[73] Assignee: BASF Aktiengesellschaft, Ludwigshafen, Fed. Rep. of Germany

[21] Appl. No.: 341,471

[22] Filed: Apr. 21, 1989

[30] Foreign Application Priority Data

May 4, 1988 [DE] Fed. Rep. of Germany ....... 3815050

[51] Int. Cl.$^5$ .............................................. C07C 147/10
[52] U.S. Cl. ....................................... 568/33; 528/171
[58] Field of Search ........................... 568/33; 528/171

[56] References Cited

U.S. PATENT DOCUMENTS 3,419,624 12/1968 Cotter et al. ........................ 528/174
3,536,734 10/1970 Vegter et al. .

FOREIGN PATENT DOCUMENTS 1259880 2/1968 Fed. Rep. of Germany .

OTHER PUBLICATIONS

J. Rivkin et al., Ind. Eng. Chem., vol. 30 (1938) p. 1228.
S. P. Panda et al., J. Polym. Sci., Polym. Letters Ed., vol. 24, 403–412 (1986).

Primary Examiner—Mary E. Ceperley
Attorney, Agent, or Firm—William G. Conger

[57] ABSTRACT

Novel phenol compounds of the general formula

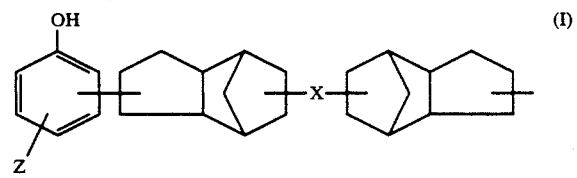

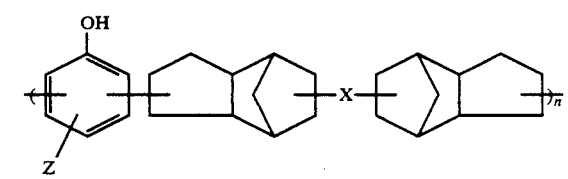

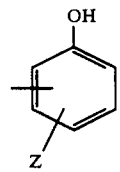

where X is a sulfone group or contains a sulfone group, are suitable for the preparation of epoxy resins, vinyl ester resins, bismaleimide resins and cyanate resins.

12 Claims, No Drawings

NOVEL POLYPHENOL AND THERMOSETTING PLASTICS PREPARED THEREFROM

The present invention relates to a novel polyphenol and to thermosetting resins which can be prepared therefrom.

Thermosetting resins, for example epoxy, vinyl ester, bismaleimide or cyanate resins, based on conventional polyphenols, for example on bisphenol A, have good mechanical properties after curing but their heat stability is insufficient for certain applications. If polyphenols, which are obtainable by condensation of dicyclopentadiene (DCPD) with phenol, for example according to U.S. Pat. No. 3,419,624, are used as starting materials for the abovementioned thermosetting resins, the corresponding cured polymers have excellent heat stability but are brittle owing to the relatively high crosslinking density.

It is an object of the present invention to provide novel polyphenols which can be converted into thermosetting resins, such as epoxy, vinyl ester, bismaleimide or cyanate resins, having high heat stability and good mechanical properties.

We have found that this object is achieved by the novel polyphenol compounds. In the general formula, Z is preferably H and X is preferably $SO_2$ or $SO_2$—$CH_2$—$CH_2$—$SO_2$, and n is, in particular, from 0 to 1.

1. Preparation of the polyphenol compounds

The reaction of hydrogen sulfide with dicyclopentadiene is known (German Pat. No. 1,259,880). The starting materials react in the presence of a free radical catalyst to give bis-(dihydrodicyclopentadienyl) sulfide. Dithiols also react under the same conditions. Thus, ethylenebis-(dihydrodicyclopentadienyl) sulfide is obtained from, for example, dithioglycol and DCPD. The addition of the thiol group takes place only at the double bond in the bridged 6-membered ring of the DCPD. The oxidation of the sulfides to sulfones is advantageously carried out using hydrogen peroxide in glacial acetic acid. The remaining double bond in the 5-membered ring of the DCPD is reacted with phenol in a subsequent acid-catalyzed reaction. Reactions of DCPD with phenols are described in the literature (for example J. Rivkin and W. E. Sheehan, Ind. Eng. Chem. 30 (1938), 1228; S. P. Panda and S. D. Kakade, J. Polym. Sci., Polym. Lett. Ed. 24 (1986), 403). Ethers are formed at low temperatures (kinetic reaction control), while C—C bonds are formed at higher temperatures (thermodynamic reaction control).

In addition to phenols, it is also possible to use other hydroxyl-containing aromatic compounds, provided that one or more ortho or para ring positions in relation to the hydroxyl group are free. Examples are chlorophenol, bromophenol, methylphenol, hydroquinone, pyrocatechol, resorcinol, pyrogallol, isopropylphenol, ethylphenol, propylphenol, tert-butylphenol, isobutylphenol, phenylphenol, bisphenol A and dihydroxydiphenyl sulfone.

2. Epoxy resins

The epoxy resins based on the polyphenol compounds I are obtained by reaction with epoxyalkyl halides, preferably epichlorohydrin.

Reaction of the epoxyalkyl halides with the polyphenol compound can be carried out both in one step and as a two-stage reaction with isolation of the chlorohydrin ether intermediate. The usual epoxidation catalysts, such as ammonium, phosphonium or arsonium salts, are used. The dehydrohalogenation is carried out in the presence of a base, e.g. potassium carbonate, aqueous sodium hydroxide solution or potassium hydroxide solution. Some, preferably less than 40 mol %, of the polyphenol compound may be replaced with conventional polyphenols, e.g. bisphenol A.

The novel epoxy resins can be used directly for the production of molded materials, for example production mouldings, fiber-reinforced materials, coatings and adhesives. For this purpose the conventional curing agents, alone or together with curing accelerators, are added to the epoxy resins, in amounts from 1 to 150, preferably from 3 to 100, parts by weight per 100 parts by weight of epoxy resin, and are cured at elevated temperatures. Suitable curing agents are polyamines, polycarboxylic anhydrides and catalytic curing agents, for example hydrazides. Bis-(4-aminophenyl)-methane, bis-(4-aminophenyl) sulfone, bis-(4-aminophenyl) ketone and dicyanodiamide are particularly preferred. Conventional additives, such as reinforcing fibers of glass or carbon, fillers, plastics and metal powders, can be mixed with the epoxy resins. The molded materials obtained on curing possess good resistance to chemicals and high heat distortion resistance. In contrast to epoxy resins based on bisphenol A or to the resins based on dicyclopentadiene/phenol adducts according to U.S. Pat. No. 4,390,680, the epoxy resins based on the novel polyphenol compound have the advantage of low water absorption and improved toughness.

3. Vinyl ester resins

The epoxy resins based on the polyphenol compound I can be used for the preparation of corresponding vinyl ester resins.

For this purpose, they are reacted with unsaturated monocarboxylic acids. Preferred monocarboxylic acids are acrylic acid, methacrylic acid and half esters of unsaturated dicarboxylic acids, for example of maleic acid. The reaction is carried out in the absence of a catalyst, in the presence of a Lewis base, for example a tertiary amine, a triarylphosphine, an acetate, an alcoholate or an ammonium halide, at from 60° to 130° C. in an inert solvent or in the melt. From 0.6 to 1.1 equivalents of the unsaturated monocarboxylic acid are preferably used per epoxy group. In the preparation of the vinyl esters, some, preferably less than 40 mol %, of the novel epoxy resin can be replaced with conventional epoxy resins, for example those based on bisphenol A or on novolaks.

The vinyl ester resins contain

A. from 25 to 100% by weight of the vinyl esters described,

B. from 0 to 75% by weight of an unsaturated monomer which is copolymerizable with A, and C. conventional additives.

Suitable copolymerizable, ethylenically unsaturated monomeric compounds are the allyl and, preferably, vinyl compounds usually used for the preparation of unsaturated vinyl ester resins, for example vinylaromatics, such as styrene, substituted styrenes, such as p-chlorostyrene, or vinyltoluene, esters of acrylic acid and methacrylic acid with alcohols of from 1 to 18 carbon atoms, such as methyl methacrylate, butyl acrylate, ethylhexyl acrylate, hydroxypropyl acrylate, dihydrodicyclopentadienyl acrylate or butanediol acrylate, and (meth)acrylamides, allyl esters, such as diallyl phthalate, and vinyl esters, such as vinyl ethylhexanoate, vinyl acetate, vinyl propionate, vinyl pivalate, etc. Mixtures of the stated olefinically unsaturated monomers are also suitable. Preferred components II are styrene, α-methylstyrene, chlorostyrene, vinyltoluene, divinylbenzene and diallyl phthalate.

The vinyl ester resins prepared according to the invention can also be cured without dilution with an unsaturated monomer, in the presence of a polymerization initiator. Usually, however, they are diluted with from 0 to 75, preferably from 25 to 75, % by weight of a copolymerizable, ethylenically unsaturated compound. Furthermore, solutions of the monomer-free vinyl esters in nonpolymerizable solvents can be used for the production of prepregs and for coating purposes.

Conventional polymerization initiators are peroxides and other organic compounds which form free radicals at elevated temperatures the amounts used being from 0.05 to 5, preferably from 0.1 to 3, by weight, based on the total weight of components A+B. Examples of free radical initiators are benzoyl peroxide, tert-butyl peroctoate, tert-butyl perbenzoate, cyclohexanone peroxide, tert-dibutyl peroxide and hydroperoxides, as well as azo compounds, such as azobisiso butyronitrile, and organic compounds having a labile carbon-carbon bond. When conventional photoinitiators, for example benzoin ethers, benzil ketals or acylphosphine oxide compounds, are used, curing can be carried out by exposure to light having a wavelength of from 200 to 500 nm.

Examples of suitable fillers are conventional finely powdered or particulate inorganic fillers, such as chalk, kaolin, powdered quartz, dolomite, barite, metal powders, cement, talc, kieselguhr, woodmeal, wood chips, pigments and the like. Suitable reinforcing fibers are those consisting of glass, carbon or aromatic polyamide. They are used in amounts of from 20 to 200% by weight, based on A +B.

The novel vinyl ester resins are preferably cured to give fiber-reinforced moldings which have both high heat stability and good toughness.

4. Bismaleimide resins

The polyphenol compounds I can furthermore be allylated to give polyallylphenols or polyallyl ethers II, which are used as curing components (comonomers) for bismaleimides.

Preferably, the polyphenols of the subject invention correspond to the formula:

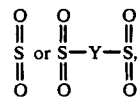

Y is an alkylene or arylene group of not more than 15 carbon atoms and Z is H, halogen, OH, alkyl aryl, O-alkyl, O-aryl

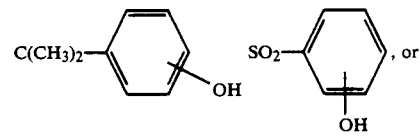

IIA: R=allyl and R'—H
IIB: R=H and R'=allyl

The allylated derivatives II are obtained by reacting the polyphenols I with unsubstituted or substituted allyl halides, for example according to DE 2 818 091. Suitable allyl halides are allyl chloride, allyl bromide, methallyl chloride and methallyl bromide, allyl chloride being preferred. The substituents Z must be inert to allyl halides and not undergo reaction with the latter.

The corresponding O-allyl ethers IIA (R'=H and R=allyl) initially obtained can be converted into the corresponding allylphenols IIB (R'=allyl and R=H) in a Claisen rearrangement reaction (according to DE No. 2 818 091).

Bismaleimide resins are obtained by reacting an allyl compound II with a bismaleimide of the general formula

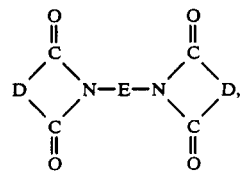

where D is an unsubstituted or substituted carbon-carbon double bond and E is a divalent radical of not less than two carbon atoms. Bismaleimides are disclosed in, for example, DE-A-2 040 094, DE-A-2 719 903 and DE-A-3 247 058. In addition to bismaleimides,

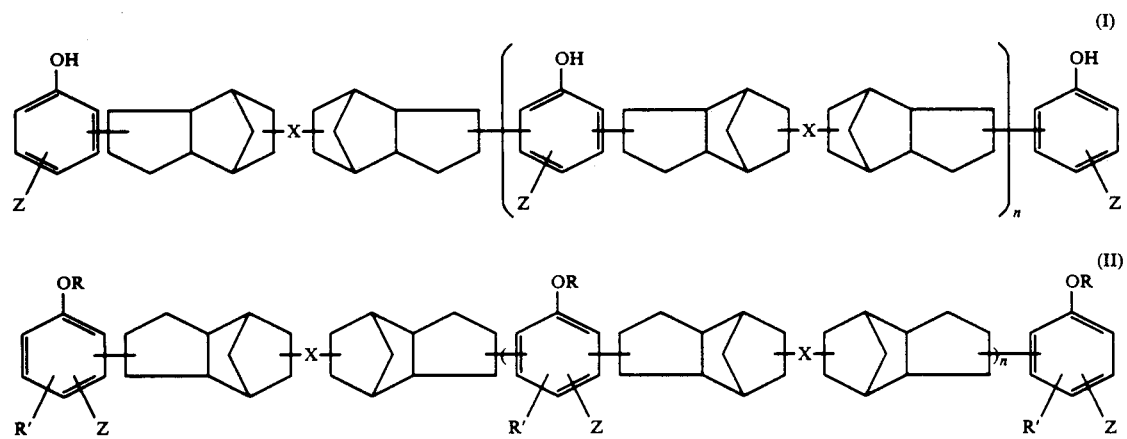

where n is on the average from 0 to 5, polymaleimides and mixtures of various bismaleimides are in principle also suitable. Preferred bismaleimides are 4,4,40-bismaleimidodiphenylmethane, 4,4,40-bismaleimidodiphenyl ether, 3,3,40-bismaleimidodiphenyl sulfone, 1,3-bismaleimidobenzene, 2,4-bismaleimidotoluene, 1,6-bismaleimidohexane and 2,2,4-trimethyl-1,6-bismaleimidohexane. Up to 20% by weight of a monoimide may also be present.

The mixing ratio in the reaction of the bismaleimide with the allyl compound can be chosen relatively freely, a ratio of 1 equivalent to 0.05 to 5 equivalents being preferred. It is assumed that the reaction involves not only copolymerization which is presumably initiated by free radicals but also reactions of the addition type, for example en reactions and Diels-Alder reactions.

Depending on the intended use, it may be advantageous to add further components to the novel resins. For example, conventional epoxy resins or vinyl ester resins are suitable.

Other additional components which may be used are amines, preferably aromatic diamines (e.g. 4,4'-diaminodiphenylmethane) and aminophenols, which may likewise undergo an addition reaction with the maleimido double bonds. Prepolymers, for example those obtained from a bisimide and an amine, can also be used.

For certain uses, it may be advantageous to employ suitable vinyl monomers, e.g. styrene, α-methylstyrene, divinylbenzene, acrylates or methacrylates, diallyl phthalate, 3,3',-diallylbisphenol A, triallyl isocyanurate, triallyl cyanurate or vinylpyrrolidone, to obtain a desired viscosity. The amount of these may be up to 50% by weight, based on the mixture.

The mixtures may contain catalysts or inhibitors as further additives. Suitable catalysts are tertiary amines or phosphines, imidazoles or organic acids or peroxides. Examples of inhibitors are hydroquinone, benzoquinone and phenothiazine. The amount of initiators and inhibitors used should be about 0.05-1.5% by weight.

The mixtures may contain further additives which are conventionally used in the technology of curable plastics, e.g. fillers, plasticizers, pigments, dyes, mold release agents and flame-retardant substances. It is also possible to use glass fibers, carbon fibers, graphite powder, mica, quartz powder, kaolin or metal powder as fillers, in amounts of up to 80% by weight, based on the mixture.

The novel mixtures can be used as impregnating, casting and laminating resins or as molding materials (with or without fillers).

If they are used for the production of high-performance reinforced materials, the impregnation of glass fibers, carbon fibers or aramid fibers can be carried out with the formation of unidirectional or fabric prepregs, either from the melt at 50°-150° C. or from solution. Suitable solvents are halohydrocarbons, e.g. dichloromethane, ketones, e.g. acetone or methyl ethyl ketone, glycol esters, toluene, dimethylformamide, N-methylpyrrolidone or mixtures of a plurality of solvents.

To prepare the bismaleimide resins, the starting materials are mixed using a conventional method and are heated to 70°-190° C., a prepolymer being formed. Depending on the progress of the prepolymerization, a highly viscous melt or a glassy solid is obtained, the product being milled or dissolved in a solvent, depending on the intended use. Preparation of the resins can also be carried out in one of the abovementioned solvents.

The resins are cured at about 100°-300° C., under atmospheric or superatmospheric pressure, preferably at from 160° to 260° C. The curing temperature chosen depends decisively on the length of the curing time and vice versa. Stepwise curing is frequently advantageous, crosslinking of the polymers being effected at a relatively low temperature, initially with shaping. After removal from the mold, postcuring at above 200° C., which may last for several hours, can then be carried out to effect complete curing.

The resins can be used to produce high-performance engineering materials, for example insulating materials, structural components, apparatus housings and electrical components, which are exposed to high temperatures.

5. Cyanate resins

Novel cyanate resins can furthermore be prepared from the polyphenol compounds I by reaction with a cyanogen halide. For example, the procedure described in U.S. Pat. No. 4,026,913 is adopted, in which a polyphenol and cyanogen bromide in a solvent, preferably acetone, are initially taken and the reaction is carried out by adding a base, e.g. triethylamine. Instead of cyanogen bromide, it is also possible to use cyanogen chloride. The cyanate resins thus obtained can be cured by a generally known method, alone or as a mixture with other cyanate resins, for example those based on bisphenol A, or with epoxy resins or with bismaleimides, to give heat-resistant thermosetting plastics. Suitable curing catalysts are metal compounds or tertiary amines. The Sn, Fe, Co, Ni, Cu and Zn salts of organic acids, for example the acetylacetonates, octoates or naphthenates, are preferred. Curing is carried out at 150°-250° C.

The thermosetting plastics which can be prepared from the polyphenols I possess not only good mechanical properties but also excellent heat resistance. They can be used for the production of molded materials, for example of moldings, fiber-reinforced materials, coatings and adhesives.

EXAMPLES

Preparation of a polyphenol (a) Bis-(dihydrodicyclopentadienyl) sulfide 1,188 g of DCPD and 23.8 g of azobisisobutyronitrile are heated to 60° C. in a 2 1 four-necked flask provided with a stirrer, a gas inlet tube, a thermometer and a reflux condenser. 168 g of $H_2S$ are passed in over a period of 10 hours. An exothermic reaction initially takes place, and the temperature should not exceed 80°-85° C. After 5 hours, a further 11.9 g of azobisisobutyronitrile are added. After the end of the passage of $H_2S$, stirring is continued for a further 4 hours at 85° C. Low molecular weight components are removed under 20 mmHg, the temperature being increased to 170° C. 1,270 g of a yellow, viscous liquid remain (91.2% of theory). (b) Bis-(dihydrodicyclopentadienyl) sulfone.

1,030 g of bis-(dihydrodicyclopentadienyl) sulfide and 2,060 g of glacial acetic acid are initially taken in a 6 1 flask. The solution is heated to 70°-80° C., and 494 g of $H_2O_2$ (50% strength) are added dropwise in the course of 3.5 hours. Stirring is then continued for a further 4 hours at 75° C. After the mixture has cooled room temperature, $H_2O$ is slowly added until crystallization begins (about 70 ml). The mixture is cooled to 10° C., and the product is filtered off, washed thoroughly with H₂O and dried at 60° C. in a drying oven under reduced pressure. 810 g of a pale yellow powder remain (71% of theory).

(c) Polyphenol based on bis-(dihydrodicyclopentadienyl) sulfone 760 g of bis-(dihydrodicyclopentadienyl) sulfone, 1,600 g of phenol and 575 g of Lewatit SPC 118H+ (Bayer, acidic ion exchanger) are slowly heated to 110° C. in a 6 l flask and stirred for 24 hours at this temperature. The mixture is cooled to 80° C. and the ion exchanger is filtered off and washed with phenol. Phenol and other volatile components are removed by distillation under reduced pressure (200° C., 1 mbar).

| Weight of product | 850 g (71% of theory) |
|---|---|
| Appearance | dark red to violet |
| Softening point (Kofler) | 125° C. |
| Elemental analysis | theoretical value for bifunctional compound |
| C   72.2% | 74.1 |
| H   7.9% | 7.4 |
| O   11.0% | 12.3 |
| S   8.0% | 6.2 |

2. Preparation of an epoxy resin 400 g of the polyphenol compound 1c in 2,150 g of epichlorohydrin are gently refluxed. 106 g of 50% strength sodium hydroxide solution are then metered in. The azeotrope consisting of epichlorohydrin and water is distilled off continuously from the reaction vessel so that the water concentration is kept at about 1%. After the alkali has been fed in (2 hours), the reaction is continued for a further 30 minutes, after which the mixture is cooled to 80° C. and 500 ml of water are added. After phase separation, the organic layer is washed twice with water and then freed from the excess epichlorohydrin in a thin film evaporator (170° C., 3 mbar).

The reddish brown epoxy resin has a softening point of 66° C. and an epoxide equivalent weight of 370.

3. Preparation of a vinyl ester resin 0.2 g of hydroquinone monomethyl ether and 0.5 g of benzyltriethylammonium chloride are added to 370 g of the epoxy resin from Example 2 and the mixture is heated to 120° C. 86 g of methacrylic acid are added in the course of 10 minutes and the mixture is heated at 105°–110° C. for 6 hours. During this procedure, about 95% of all epoxy groups are converted, and the course of the reaction is monitored by measuring the acid number. The resulting vinyl ester is dissolved in 304 g of styrene at 100° C. The solution formed has a viscosity of 450 mPa.s at room temperature.

2.0% of methyl ethyl ketone peroxide and 1% of cobalt naphthenate (1% strength in styrene) are stirred, at 23° C., into the solution of resin in styrene, described in the above section, and the mixture is cured to give a 4 mm thick pure resin sheet (2 hours at room temperature, 20 hours at 160° C.).

The following properties were measured:

| Tensile modulus of elasticity | 3,600 N/mm² |
|---|---|
| Tensile strength | 57 N/mm² |
| Elongation at break | 3.2% |
| Glass transition temperature | 156° C. |

4. Preparation of a bismaleimide resin (a) Allylation of the polyphenol 1c

The mixture of 158 g of polyphenol according to (c), 22 g of sodium hydroxide and 1,000 ml of n-propanol is heated to about 90° C. and 45 ml of allyl chloride are added dropwise in the course of 1 hour. The mixture is stirred under reflux for a further 10 hours and cooled, after which the precipitated sodium chloride is filtered off. After the solvent has been distilled off, 170 g of the corresponding O-allyl ether remain as a highly viscous oil having a viscosity of 2,500 mPa.s at 100° C.

(b) Claisen rearrangement reaction of the allyl ether 155 g of the allyl ether according to 4(a) are heated at 200° C. for 3 hours under about 1 mbar. 149 g of allylphenol are obtained as a reddish brown, highly viscous resin which solidifies at room temperature; softening point: about 65° C. (Kofler hot stage); viscosity at 125° C.: 3,200 mPa.s.

(c) Preparation of a bismaleimide resin from allylphenol 280 g of 4,4'-bismaleimidodiphenylmethane are added, a little at a time, to 120 g of allylphenol according to (b) and 0.8 g of 2,6-dimethylhydroquinone in a reaction vessel, at a bath temperature of 160° C., while stirring. The low-viscosity resin material is heated for 10 minutes and then further processed as follows:

1. A small proportion of the resin is poured onto a metal foil to achieve more rapid cooling. After it has cooled, the reddish brown resin has a softening point of 50° C. (Kofler hot stage); its gelling time at 160° C. is 38 minutes.

2. The remaining part of the resin material is poured into 1 mm and 4 mm thick metal molds and cured for 2 hours at 160° C., for 5 hours at 190° C. and for 8 hours at 240° C. The polymer has a glass transition temperature above 300° C. (according to DIN 53,455); at 325° C., it still has 50% of its room temperature shear modulus (according to DIN 53,455); modulus of elasticity: 3,990 N/mm² $^{1 \, (DIN \, 53,457)}$.

5. Preparation of a cyanate resin 55.2 g of triethylamine are added dropwise at 0° C. in the course of 30 minutes to a solution of 143.6 g of polyphenol according to Example 1c), and 100 ml of a 5 molar solution of cyanogen bromide in acetonitrile in 1,000 ml of acetone. The mixture is stirred for a further 2 hours at 0° C., the precipitated triethylammonium bromide is thawed out and the mixture is then filtered. The mother liquor is evaporated down under reduced pressure and the residue is dissolved in 2 l of dichloromethane. The solution is then washed with a large amount of water, dried over sodium sulfate and evaporated down under reduced pressure at no higher than 30° C. 104 g (67%) of a cyanate resin having a softening point of 45° C. (Kofler hot stage) are obtained; IR (KBr): 2,240, 2,260 cm⁻¹ (-OCN).

After the addition of 0.05% of cobalt naphthenate and curing for 2 hours at 170° C. and for 12 hours at 220° C., a polymer having a glass transition temperature of 224° C. is formed.

We claim:

1. A polyphenol compound having the structure

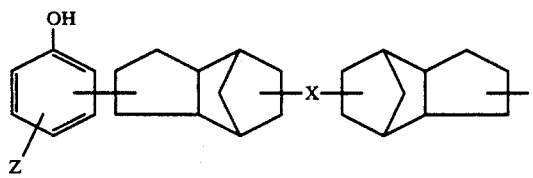 (I)

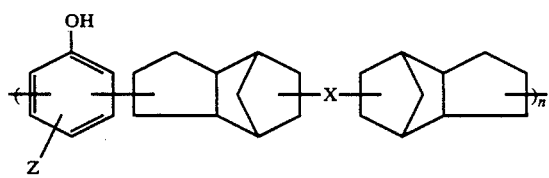

where n is on average from 0 to 5 and

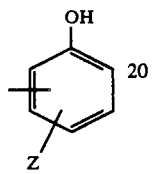

y is an alkylene or arylene group of not more than 15 carbon atoms and Z ios H, Hal, OH, alkyl, aryl, O-alkyl, O-aryl,

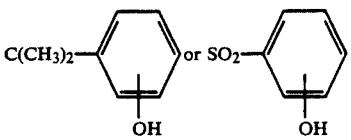

2. The polyphenol of claim1 wherein n is 0 or 1.
3. The polyphenol of claim 1 wherein X is

4. The polyphenol of claim 2 wherein X is

5. The polyphenol of claim 1 wherein Z is H, aryl, or alkyl.
6. The polyphenol of claim 2 wherein Z is H, aryl, or alkyl.
7. The polyphenol of claim 3 wherein Z is H, aryl, or alkyl.
8. The polyphenol of claim 4 wherein Z is H, aryl, or alkyl.
9. The polyphenol of claim 2 wherein Z is H.
10. The polyphenol of claim 2 wherein Z is H.
11. The polyphenol of claim 3 wherein Z is H.
12. The polyphenol of claim 4 wherein Z is H.

* * * * *